United States Patent
Velander et al.

(10) Patent No.: US 6,194,552 B1
(45) Date of Patent: Feb. 27, 2001

(54) IMMUNOSORBENTS WITH DEVELOPED BINDING EFFICIENCY AND METHOD OF MANUFACTURE

(75) Inventors: William H. Velander, Blacksburg, VA (US); Carolyn Orthner, Kennsington, MD (US)

(73) Assignee: Center for Innovative Technology, Herndon, VA (US)

( * ) Notice: Subject to any disclaimer, the term of this patent is extended or adjusted under 35 U.S.C. 154(b) by 0 days.

(21) Appl. No.: 08/293,374

(22) Filed: Aug. 19, 1994

Related U.S. Application Data (63) Continuation of application No. 07/614,663, filed on Nov. 16, 1990, now abandoned.

(51) Int. Cl.[7] .......................... C07K 17/08; C07K 17/12; C07K 17/14; G01N 33/543
(52) U.S. Cl. .......................... 530/413; 435/7.5; 435/7.92; 436/527; 436/528; 436/530; 436/531; 436/815; 436/823; 436/828; 530/391.1
(58) Field of Search .............................. 530/413, 391.1; 435/7.5, 7.92; 436/527, 528, 530, 531, 815, 823, 828

(56) References Cited

PUBLICATIONS

Tharakan, et al., *J. Chromatography*, 522, pp. 153–162 (1990).
Velander, et al., *Biotechnology and Bioengineering*, vol. 39, pp. 1013–1023 (1992).
Steers, Jr., et al., *J. Biol. Chem.*, vol. 246, No. 1, 196–200 (1971).
Lowe, et al., *Biochem. J.*, 133, 499–506 (1972).
Cuatrecasas, *J. Biol. Chem.*, vol. 245, No. 12, pp. 153–162 (Jun. 25, 1970).
Goding, *Monoclonal Antibodies: Principles and Practice* pp. 218–240 (1986).
O'Shannessy, et al., *J. Appl. Biochem.*, 7, 347–355 (1985).
Comoglio, *Biochimica et Biophysica Acta*, 420, 246–257 (1976).
Eveleigh, *J. Solid–Phase Biochem.*, 2(1), 45–77 (1977).
Gersten, *J. Immunol. Meth.*, 24, 305–309 (1978).
Nose, *Proc. Natl. Acad. Sci.*, 80, 6632–6636 (1983).
Sox, *Proc. Natl. Acad. Sci.*, 66(3), 975–982 (1970).
Wallick, *J. Exp. Med.*, 168, 10–99–1109 (1988).
Schneider, *J. Biol. Chem.*, (18), 10766–10769 (1982).
Akerstrstrom, *J. Immunol.*, 135, 2589–2592 (1985).
O'Shannesy, *J. Immunol. Methods*, 99, 153 (1987).
Babashak, *J. Chromatogr*, 444, 22 (1988).
Sato, *Appl. Biochem. Biotech.*, 15, 145–158 (1987).
Stearns, *J. Biol. Chem.*, 63(2), 826–832 (1988).
Orthner, *J. Biol. Chem.*, 264, 310 18781–18788 (1989).
Sakuragawa, *Thrombosis Research*, 41, 627 (1986).
Berger, *Blood*, 71, 1641–1647 (1988).

*Primary Examiner*—Mary E. Ceperley
(74) *Attorney, Agent, or Firm*—Whitham, Curtis, Whitham & McGinn (57) ABSTRACT

The antitope of an antibody is masked with a masking agent, followed by immobilization on a support. The masking agent is then eluted to produce an improved immunosorbent, which is capable of binding more than double the amount of an antigen than existing immunosorbents having the same antibody bound at the same density. Preferably, the masking agent is an antigen or other compound having an epitope for which the antitope of the bound antibody has an avidity. In a preferred embodiment, greater than 30% of the bound antibodies maintain the same vicinity as when unbound for specific antigen or hapten molecules. Preferably, the support is formed of any conventional immunosorbent support material which allows the bound and unbound antibody to maintain an avidity for the same compounds or antigens. In a preferred embodiment, the support is formed of agarose, cellulose, piezo crystals, microtiter plates, or other materials which will not reduce the avidity of a bound antibody for an antigen in comparison to the avidity of the unbound antibody for the same antigen. Preferably, the masked antibodies are bound to supports which are activated with a reagent, such as, but not limited to, cyanogen bromide, carbonyldiimidazole, N-hydroxysuccinimide, hydrazine, hydrazide, and toluene sulfonylchloride. In another preferred embodiment, masked antibody complexes are immobilized through affinity complexing to proteins bound to a support.

9 Claims, 7 Drawing Sheets

IMMUNOSORBENTS WITH DEVELOPED BINDING EFFICIENCY AND METHOD OF MANUFACTURE

This is a continuation of U.S. patent application Ser. No. 07/614,663 filed Nov. 16, 1990, abandoned.

FIELD OF THE INVENTION

This invention is directed to immunosorbents for use in biochemical processes, such as the purification of proteins or for immunodiagnostics, and is directed more particularly to immunosorbents having immobilized antibodies oriented so as to have increased immunosorbent activity or capacity.

BACKGROUND OF THE INVENTION

Immunosorbents are useful in biochemical processes and applications, such as the isolation and purification of proteins, immunodiagnostics, and as sensors for detecting the presence of biochemical substances. Immunosorbents are capable of isolating and purifying both proteins and haptens present in complex mixtures at extremely low concentrations. [Generally, proteins are polymers formed from at least one hundred amino acid residues joined by amide linkages, and peptides are comprised of from two to ten amino acid residue joined through amide linkages; for the sake of simplicity, the term protein is used hereinafter to describe any molecule containing two or more amino acid residues joined through amide linkages. Haptens are non-proteinaceous molecules which have a sufficiently recognizable chemical structure that an antibody will have an avidity for the compound.]

Immunosorbents are generally made by immobilizing an antibody on a suitable support (also referred to as a substrate or matrix), such as a gel, membrane or other suitable chromatographic support material. Since antibodies have both high specificity and binding affinity for particular antigen or hapten molecules, immunosorbents are frequently used to separate and purify specific antigen or hapten molecules from dilute solutions thereof by interaction with immobilized antibodies on the immunosorbent matrix. Immunosorbents are also used in immunodiagnostics to assay quantities and types of proteins present in biological and biochemical samples. Of course, other uses of immunosorbents are known or will be apparent to those of skill in the art.

The total binding capacity of an immunosorbent is determined by the number of active antigen binding sites; unfortunately, only a small fraction of the antibodies immobilized on the matrix of currently available immunosorbents are "active" (i.e., able to bind to antigens). It is believed that interactions between the antigen binding site (antitope or $F_{ab}$) on the antibody and the support interfere with the ability of the bound antibody to attract and bind antigens which can be bound when the antibodies are not bound.

Typical immunosorbents, having antibodies bound directly to a matrix, bind less than 30% of the theoretical capacity of antigen or hapten molecules based on a 1:2 stoichiometry of antibody to antigen. [In other words, less than 30% of the bound or immobilized antibodies are oriented so as to have an avidity for antigens having the same epitope as the antigens eluted therefrom]. This results in a great waste of bound antibody, and requires the use of much larger quantities of immunosorbent material to achieve good separation and purification of desired compounds.

According to Cuatrecasas, the use immunosorbents, (immunoadsorbents) for the purification of antibodies or antigens is related to affinity chromatography. See "Protein Purification By Affinity Chromatography," *J. Bio. Chem,* Vol. 245, No. 12, Jun. 25, 1970, pp. 3059–3065. Both technologies involve the separation of specific molecules or bioaffinants from solutions through attraction to and binding by specific molecular recognition sites on stationary bioaffinity ligands attached to a support. In the case of immunosorbents, generally, the bound ligand is an antibody, and the specific molecular recognition sight on the antibody is referred to as an antitope; antigens for which the antitope of the antibody has an avidity for are said to contain the epitope for the antibody antitope. In certain instances, it is possible to synthesize the epitope for a given antitope of an antibody. This is especially useful when the antigen is expensive, in short supply, or difficult to work with.

Cuatrecasas has attributed the limited success of immunosorbents in purifying antibodies and antigens on the lack of suitable solid supports for the attachment of ligands, and on the failure to fix these ligands at a sufficient distance from the matrix backbone. Therefore, it was proposed that bioaffinity matrices and immunosorbents be prepared with the ligand groups (antibodies), critical in the interaction with the macromolecule to be purified (antigen), sufficiently distant from the backbone of the solid matrix to minimize allosteric (steric) interference with affinity processes. Hence, a "spacer arm" was used to attach ligands to a solid support; the spacer arm maintains the bound or immobilized ligand at a sufficient distance from the solid matrix so as to minimize matrix effects on the binding ability of the bound ligand. However, the use of such spacer arms increases the cost and difficulty of producing bioaffinity matrices and immunosorbents.

Immobilization of an antibody on an immunosorbent matrix is usually achieved by interaction between the antibody and the matrix. Frequently, a matrix is activated so that the matrix readily binds to reactive amine functional groups in the protein chain forming the antibodies. Thus, the antibodies are bound to the matrix and immobilized.

For example, Goding discloses that reactive groups such as cyanogen bromide (CNBr), N-hydroxysuccinimide, carbonyldiimidazole, and toluene sulphonylchloride can be used to activate a matrix, and the activated matrix can then be used to immobilize antibodies through accessible primary amino groups on the protein chain forming the antibody. See *Monoclonal Antibodies: Principles And Practice,* Academic Press, New York (1983). Because amino groups can be present on various parts of the protein chain (or chains) forming the antibodies, the orientation of proteins immobilized in this way on activated matrices is thought to be random on the immunosorbent support matrix surface. Thus, a significant portion of the distribution of orientations of antibodies on the immunosorbent surface obtained by random amino-coupling chemistry can be expected to lower avidity and/or completely obstruct the antigen-combining sites. Thus, attempts to follow the suggestions of Cautrecasas, discussed above, by adding a "spacer arm" between an immunosorbent support matrix and a bound antibody have not been successful in increasing the activity of immunosorbents. It is believed that a significant portion of the bonds between the "spacer arms" and the bound antibodies interfere with the ability of the bound antibodies to attract and bind antigens.

For example, O'Shannessy et al, in "Specific Conjugation Reactions Of The Oligosaccharide Moieties Of Immunoglobulins," *J. Appl. Biochem.,* 7, 347–355 (1985), discloses that immunoaffinity supports can also be prepared by coupling the carbohydrate moieties of certain antibodies to a matrix. For example, a polyclonal IgG (immunoglobulin) fraction of goat anti-human albumin was coupled to AAH (agarose adipic acid hydrazide). However, this method may not be generally useful for preparing immunosorbents, since certain antibodies, such as IgG, have low carbohydrate content. Further, it is believed that immunosorbents prepared by this method will suffer the same problem as immunosorbents prepared by other techniques, such as the loss of immunologic activity due to binding of antibody through or in close proximity to the antigen binding sites and the multiple orientations of the antibody molecules on the matrix.

It is also possible to immobilize antibodies on an immunosorbent support matrix through non-covalent bonding; for example, an immunosorbent support matrix of polystyrene will form noncovalent bonds between the long alkyl chains of isoleucine in proteins. The long non-polar alkyl chains readily associate with the non-polar environment of the plastic matrix and are attached to the polystyrene matrix due to low energy forces.

For further examples of the synthesis, variety and effectiveness of immunosorbents, their applications and for additional background, see: Comoglio, S., Massaglia, A., Rolleri, E. and Rosa, A. (1976) "Factors affecting the properties of insolubilized antibodies." *Biochimica et Biophysica Acta*, 420, 246–257. Cress, M. C. and Ngo, T. T. (1989) "Site Specific Immobilization of Immunoglobulins." *Amer. Biotech. Lab.*, xx, 16–19. Eveleigh, J. W. and Levy, D. E. (1977) "Immunochemical characteristics and preparative application of agarose-based immunosorbents." *J. Solid-Phase Biochem.*, 2(1), 45–77. Gersten, D. M. and Marchalonis, J. J. (1978) "A rapid, novel method for the solid-phase derivatization of IgG antibodies for immuno-affinity chromatography." *J. Immunol. Meth.*, 24, 305–309. Tijssen, P. (1985) "Practice and Theory of Enzyme Immunoassays." Vol. 15, Elsevier, New York. Nose, M. and Wigzell, H. (1983) "Biological significance of carbohydrate chains on monoclonal antibodies." *Proc. Natl. Acad. Sci.*, 80, 6632–6636. Sox, H. C. and Hood, L. (1970) "Attachment of carbohydrate to the variable region of myeloma immunoglobulin light chains." *Proc. Natl. Acad. Sci.*, 66(3), 975–982. Wallic, S. C., Katat, E. A. and Morrison, S. L. (1988) "Glycosylation of a VH residue of a monoclonal antibody against (1–6) dextran increases its affinity for antigen." *J. Exp. Med.*, 168, 10–99–1109. Schneider, C., Newman, R. A., Sutherland, D. R. Asser, U. and Greaves, M. F. (1982) "A one-step purification of membrane proteins using a high efficiency immunomatrix." *J. Biol. Chem.*, 257 (18), 10766–10769. Akerstroström, B., Brodin, T., Reis, K. and Björck. L. (1985) "Protein G: a powerful tool for binding and detection of monoclonal and polyclonal antibodies." *J. Immunol.*, 135, 2589–2592. O'Shannesy, D. J. and Quarles, R. H. (1987) *J. Immunol. Methods*, 99, 153. Babashak, J. V. and Philips, T. M. (1988) *J. Chromatogr.*, 444, 22. Sato, H., Kidake, T. and Hori, M. (1987) "Leakage of immobilized IgG from therapeutic immunoadsorbents." *Appl. Biochem. Biotech.*, 15, 145–158. Sterns, D. J., Kurosawa, S., Sims P. J., Esmon, N. L. and Esmon, C. T. (1988) "The interaction of a $Ca^{2+}$-dependent monoclonal antibody with the Protein C activation peptide region," *J. Biol. Chem.*, 63(2), 826–832. Orthner, C. L., Madurawe, R. D., Velander, W. H., Drohan, W. N., Battey, F. D., Strickland, D. K. (1989) "Conformational changes in an Epitope Localized to the $NH_2$-terminal Region of Protein C." *J. Biol. Chem.* 264(310 18781–18788. Sakuragawa, N., Shimizu, J., Kondo, K., Kondo, S., Niwa, M. (1986) "Studies on the effect of PEG-modified urokinase on coagulation-fibrinolysis using beagles." *Thrombosis Research*, 41, 627. Berger, Jr., H. and Pizzo, S. V. (1988) "Preparation of polyethylene glycol-tissue plasminogen activator adducts that retain functional activity: characteristics and behavior in three animal species." *Blood,* 71, 1641–1647. All references discussed or mentioned above or hereafter are incorporated by reference as if reproduced in full below.

Thus, there is a need for immunosorbents with improved binding efficiency, such that a high percentage of the antibodies bound or immobilized on a support are capable of maintaining avidity sufficient to attract and bind with proteins or haptens which they are capable of binding with when not bound to a support (or otherwise complexed). There is also a need for an inexpensive process for preparing immunosorbents having improved binding efficiency. An immunosorbent with improved binding efficiency is defined hereinafter as any immunosorbent in which greater than 30% of bound antibodies or bound ligands are active; active is defined hereinafter as the ability of the specific molecular recognition site on a ligand or the ability of the antitope on an antibody to be able to attract and bind to compounds or antigens.

SUMMARY OF THE INVENTION

Immunosorbents with improved binding efficiency are produced by masking the antitope of an antibody with a masking agent, followed by immobilization of the masked antibody on a support. In a preferred embodiment the masking agent is an antigen which forms an antigen-antibody complex with the antibody; the complex is subsequently immobilized on a support. Following the immobilization of a masked antibody or antigen-antibody complex on a support, the masking agent or antigen is eluted from the bound complexes immobilized on the support, leaving highly oriented antibodies immobilized on the support. Preferably, greater than 30%, and generally a minimum of 50% to 60%, of the bound antibodies are oriented properly such that they are active. In a preferred embodiment, greater than about 94% bound activity has been achieved for the immunosorbents of the present invention. Preferably the support is formed of agarose, cellulose, piezo crystals, microtiter plates, synthetic polymers, natural polymers, and inorganics; the support or matrix can also be formed of any other chromatographic support material or any material which is capable of binding directly to an antibody, or of being "activated" to bind to an antibody, without interfering with the avidity of the bound antibody for proteins or haptens, which the unbound antibody would have an avidity for. Preferably, the support material will not interfere with the application to which the immunosorbent is being used. The masked antibodies or antigen-antibody complexes are preferably bound to the supports through conventional amine or carbohydrate coupling chemistry, through other covalent or low energy bonding methods, or through affinity complexing.

Preferably, the density of antibody bound to the support is sufficiently high to provide for the maximum number of active antibodies per unit area of support, while maintained at a low enough density to prevent antibody-antibody interactions, which may interfere with the ability of the bound antibodies to attract and bind the same protein and haptens that they are capable of attracting and binding when unbound.

Thus, it is a primary object of the present invention to bind or immobilize antibodies on supports in a manner which produces immunosorbents with improved binding efficiency.

It is a further object of the present invention to provide an improved method for manufacturing immunosorbents, in which greater than 30% of the bound antibodies maintain avidity for proteins and haptens for which the unbound antibodies have avidity.

DETAILED DESCRIPTION OF THE INVENTION

The present invention utilizes sterically masking or orientation-directing agents (FMAs or ODAs), which sterically mask Fab regions, prior to immobilization of monoclonal or polyclonal antibodies (Mabs or Pabs) on supports to produce immunosorbents in which the antigen-binding, $F_{ab}$, regions are oriented away from the matrix, or are in an otherwise active conformation. Antibodies are large molecules and contain many reactive residues, such as the amino groups of lysine and the N-terminus, the carboxyl groups of aspartate, glutamate and the C-terminus, and phenolic groups of tyrosines. Generally, these reactive groups are used to immobilize the antibodies on a matrix through covalent coupling of the reactive residues to a matrix which has been activated, or a coupling reagent is used to bind the reactive residues to an unactivated matrix. However, the aforementioned reactive groups on the antibodies are located in both the antigen binding, $F_{ab}$, and cell receptor, $F_c$, domains; thus, the antibody can be coupled through reactive residues in the $F_{ab}$ region, or be coupled to a matrix in an orientation that makes the $F_{ab}$ region inaccessible. It is believed that this is the primary cause for the low activity of existing immunosorbents.

The present invention is able to produce immunosorbents with improved binding efficiency through the use of ODAs, such as antigens, peptide-antigen adducts, chimeric adducts of polymers with an antigen, haptens, and a variety of other proteins and compounds.

EXPERIMENTAL METHODS AND EXAMPLES

The following non-limiting examples demonstrate the efficacy of using orientation directing antigens or masking agents for the immobilization of antibodies on supports to produce immunosorbents. It is to be understood that a wide variety of other antibodies than those mentioned herein may be bound to supports to form immunosorbents using this invention, and that a wide variety of proteins and haptens can be bound to the improved immunosorbents without requiring undue experimentation by one of skill in the art, or departure from the spirit and teachings herein.

MATERIALS

Monomeric 2-ethyloxazoline and 2-methyloxazoline were purchased from Aldrich Chemical Co., Milwaukee, Wis. A peptide, listed in the sequence listing, as Sequence ID No. 1, and corresponding to residues 6–17 of the heavy chain of human Protein C (referred to as HCPC[6–7] or the C-peptide), was made by t-boc synthesis. This is a synthetic epitope for $Ca^{2+}$-dependent murine IgG (HPC4) monoclonal antibody. Because of the $Ca^{2+}$ dependent of the binding interaction between the synthetic epitope and the antitope of HPC4-Mab, solutions containing ethylene diamine tetraacetic acid, EDTA, can be used to chelate $Ca^{2+}$ and disrupt the epitope-antitope interaction. The methyl benzhydrylamine-HCL anchoring resin for peptide synthesis was purchased from Colorado Biotechnology Associates, Boulder, Colo. HPC4 murine monoclonal antibody (HPC4-Mab or HPC4) was provided by Dr. Charles Esmon of the Oklahoma Medical Research Foundation, Oklahoma City, Okla. Rabbit antisera against human Protein C was purchased from American Bioproducts, Parsippany, N.J. Affinity purified goat, anti-mouse immunoglobulins conjugated to horseradish peroxidase (HRP) were purchased from Organon Teknika-Cappel, West Chester, Pa. Immobilon AV affinity (IAV) membranes were purchased from Millipore Corporation of Bedford, Mass. All reagents were of the best commercial grade available; it is to be understood that reagents other than those mentioned herein and having equivalent properties, may be used.

Ethyl-POX and methyl-POX C-peptide adducts were synthesized and purified by reaction of monomeric 2-ethyloxazoline and 2-methyloxazoline with benzyl iodine in acetonitrile at 90° C. to initiate and propagate polymers of varying molecular weight; following lyophilization, the polymers were terminated by reaction with C-peptide in methanol at room temperature to form polyoxazoline-peptide adducts. (POX-peptide or POX-C-peptide) of varying molecular weights. [Oxazoline polymers were prepared so as to have molecular weights, MW, of approximately 1,000, 2,000, 5,000, 10,000 and 20,000. C-peptide bound to a 1,000 MW oxazoline polymer is 1K-POX, peptide bound to a 2,000 MW POX is 2K-POX, etc . . . ].

By coupling POX to the C-peptide, one of the amino groups on the peptide is blocked, which reduces non-specific interactions between the matrix and the peptide (e.g., eliminates or reduces coupling of the antibody to the matrix in a stereochemically random fashion); this also imparts an increased size to the masking agent (peptide), and thereby, improves the masking ability of the masking agent for the antitope of the protein sought to be bound, and also helps to reduce surface density effects on the activity of the bound antibodies.

Human protein C (hPC) was isolated by immunoaffinity methods as described by Orthner et al in *J. Biol. Chem.*, 264(31) 18781–18788.

METHODS

Direct Evaluation of Total HPC4 Bound to Immobilon Membranes

The total amount of HPC4-Mab (antibody) bound to Immobilon membranes was determined by the following procedure. POX-Polymer, C-peptide, POX-C-peptide conjugates, and control samples were serially diluted in 0.50 M imidazole/0.1 M NaCl/25 mM $CaCl_2$/pH 7.0 ("Buffer A"). These samples were incubated with 0.2001 μM HPC4-Mab for 1 hour at room temperature. Control samples and samples containing ODA had the same HPC4 concentration so the amount of HPC4 spotted on the membranes was the same for all samples. A SMI "Quick-Set" micropettor was used to apply microliter, μl, quantities of each sample to the membranes in order to immobilize the masked or unmasked HPC4-Mabs thereon; spots of each sample were applied in replicates of four to Immobilon membranes, which were then wetted in phosphate buffered saline, PBS, and dried at room temperature. After drying, the IAV membranes were rewetted in PBS. The residual reactive sites on the membranes were blocked with 10% ethanolamine in 1 M $NaHCO_3$ (pH 9.4) for 2 hours at room temperature, followed by washing with 100 mM EDTA-TBS for 3 hours, with three buffer changes to remove bound POX-C-peptide conjugates or C-peptides from the HPC4-Mabs bound to the membranes. The membranes were then washed with PBS and incubated with 1:1000 diluted HRP-conjugated anti-rabbit goat antisera in PBS for 3 hours at room temperature, then washed with PBS. Bound HRP-conjugate was detected with 4-chloronaphthol substrate at $A_{570}$ using a Schimadzu CS-9000 diffuse reflectance densitometer. Total spot area was measured for each 1 $\mu$l spot of HPC4.

Determination of the Orientation Effects of ODAs on Immobilon Surfaces

Polymer, peptide, and polymer-peptide conjugates, and control samples were serially diluted in "Buffer A". These samples were incubated with 0.2001 $\mu$M HPC4-Mab for 1 hour at room temperature to produce masked and unmasked HPC4-Mab samples. Control HPC4-Mab and respective samples containing ODA had the same HPC4-Mab concentration and amount of HPC4-Mab spotted. A SMI "Quick-Set" micropettor was used to apply 1 $\mu$l of each sample in replicates of four, to Immobilon membranes, which were wetted in PBS and dried at room temperature. The spots were dried at room temperature, and the IAV membranes were rewetted in PBS. The membranes were blocked with 10% ethanolamine in 1 M $NaHCO_3$ (pH 9.4) for 2 hours at room temperature, followed by washing with 100 mM EDTA-TBS for 3 hours, with three buffer changes to remove bound polymer-peptide conjugates or peptides from HPC4-Mabs.

The membranes (protein C immunosorbents) were then incubated with 0.2001 $\mu$M hPC (human protein C) in TBS (tris-buffered saline) per 100 mM $CaCl_2$ (buffer B) for 5 hours at room temperature. In order to determine the quantity of hPC bound, the following procedure was performed: The IAV membranes were washed with buffer B, and incubated with 1:1000 diluted anti-PC rabbit antisera in PBS for 3 hours at room temperature, and washed with PBS. The membranes were then incubated with 1/1000th diluted affinity purified goat, anti-rabbit-IgG conjugated with HRP is PBS for 3 hours at room temperature, then washed with PBS. Bound HRP-conjugate was detected with 4-chloronaphthol substrate at A570 using a Schimadzu CS-9000 diffuse reflectance densitometer. Total spot area was measured for each 1 $\mu$l spot of HPC4.

Calcium Dependent Nature of HPC4 Avidity for Peptide and Adduct

An additional set of replicates were made, with the only difference being that "Buffer A" (containing a 25 mM CaCl2, and no EDTA to chelate $Ca^{2+}$) was used instead of 100 mM EDTA-TBS during the wash step. This experiment was used to verify the calcium dependent interaction of the peptide and polymer-peptide adducts with the HPC4-Mab. Failure to remove the ODA bound to HPC4 under calcium-stabilized conditions, resulted in a complete loss of signal.

Evaluation of the Avidity of "Oriented" and "Unoriented" Mab

"Oriented" and "Unoriented" immunosorbents were prepared in a manner identical to that described above in "Determination of Orientation Effects of ODAs on Immobilization." The "oriented" surfaces were prepared by pre-equilibration of C-peptide or POX-C-peptide adducts with HPC4-Mab, which masked the Fab or antitope of the HPC4-Mab, followed by immobilization on Immobilon AV membrane substrates. The unoriented Mab samples, having no pre-equilibration with peptide or polymer-peptide adduct, were likewise applied to Immobilon AV membranes.

The avidities of the immunosorbent surfaces prepared with or without the ODAs were evaluated by competitive enzyme-linked immunosorbent assay, ELISA. Identical strips of Immobilon AV membranes having replicate applications of either oriented or unoriented HPC4-Mab were incubated with different ratios of HCPC(6–17) and hPC (at a concentration of 0.2 $\mu$m hPC in buffer B) for 5 hours at room temperature. The detection of the bound hPC was performed in a manner identical to the methods used above. The half-maximal inhibition of the ELISA signal generated by the formation of HPC4-hPC complex by HCPC(6–17) was measured as a function of increasing HCPC(6–17) concentration.

EXAMPLE 1

A 1K-poly(2-ethyloxazoline) peptide adduct and free C-peptide were pre-equilibrated with HPC4-Mab at varying ratios of adduct or free peptide to antibody. A control sample of HPC4-Mab was treated in the identical fashion to the adduct and free peptide solutions, but no ODA was added. The unmasked antibody, adduct-antibody complex, and free C-peptide-antibody complex samples were bound to Immulon II surfaces, and after elution with a chelating buffer, the bound activity of the HPC4-Mabs on the Immulon II surfaces was measured. With reference to FIG. 1, a graph is presented, which compares the activity of the immunosorbents prepared with the HPC4-Mab masked or complexed with C-peptide or the 2-ethyloxazoline-peptide adduct with immunosorbents prepared without use of an ODA. The abscissa or X axis indicates the molar ratios of the ODAs or free polymer to HPC4-Mab during the equilibration or masking step. Note that the scale is logarithmic. The ordinant, or Y axis, presents the relative activity of the different immunosorbents in comparison to the activity of an immunosorbent prepared without use of an ODA; the activity of an immunosorbent prepared without use of an ODA is represented as 100%. Thus, if an immunosorbent exhibits twice the activity of an immunosorbent prepared without the use of an ODA, it would show a percent bound activity of 200%.

Figure 1:
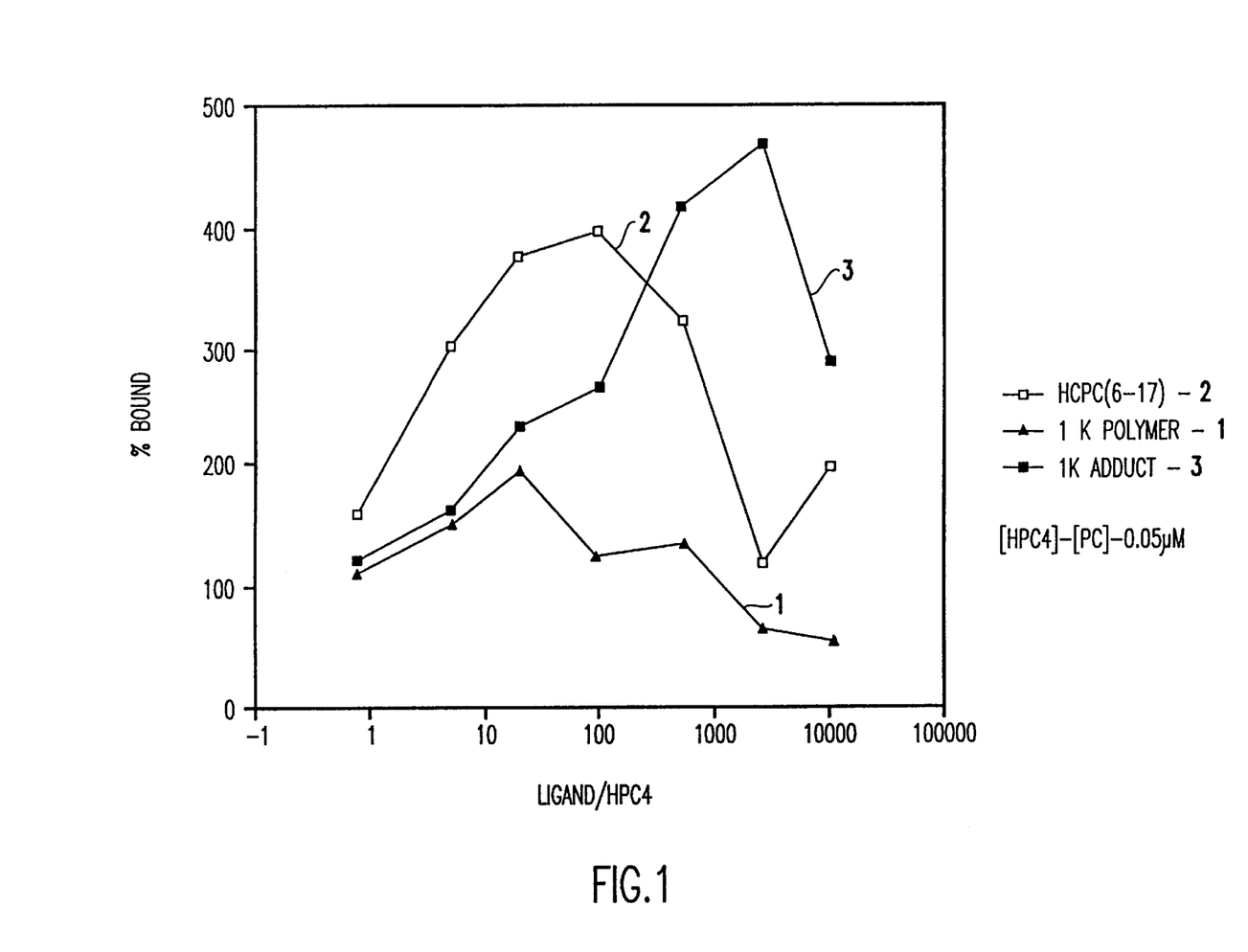
FIG. 1 is a graph comparing the activity of immunosorbents, prepared with varying molar ratios of HCPC[6–17] ODA to antibody during masking procedures, with immunosorbents prepared without use of an ODA.

Line 1 in FIG. 1 demonstrates that high molar ratios of poly(2-ethyloxazoline) to antibody in the pre-equilibration step initially results in an increase in the activity of the immunosorbents prepared, but the activity of the immunosorbents decreases below 100% as the polymer concentration increases. However, line 2, corresponding to the percent bound activity of immunosorbents prepared using the synthetic HPCP (6–17) peptide as an ODA, illustrates a dramatic improvement in the activity of immunosorbents made using the peptide as an ODA. Thus, preparation of a masking solution containing 100 moles of C-peptide to HPC4-Mab can be used to form an immunosorbent having four times the bound activity of an immunosorbent prepared without use of an ODA. Line 3 demonstrates that the poly(2-ethyloxazoline)-peptide adducts are also effective in producing immunosorbents with increased activity; However, very high molar ratios of peptide adduct to antibody must be used in the masking or equilibration step, prior to binding to a support, in order to achieve optimal percent bound activity.

Note that the immunosorbent prepared with the 1K-adduct ODA can achieve a 4.8 times greater percent bound activity than an immunosorbent prepared without use of an ODA. Compared to HCPC(6–17), the 1K-ethyl POX adduct requires a 100-fold higher molar ratio to achieve its maximum bound activity. This is consistent with its two order less avidity for the HPC4-Mab.

EXAMPLE 2

Figure 2:
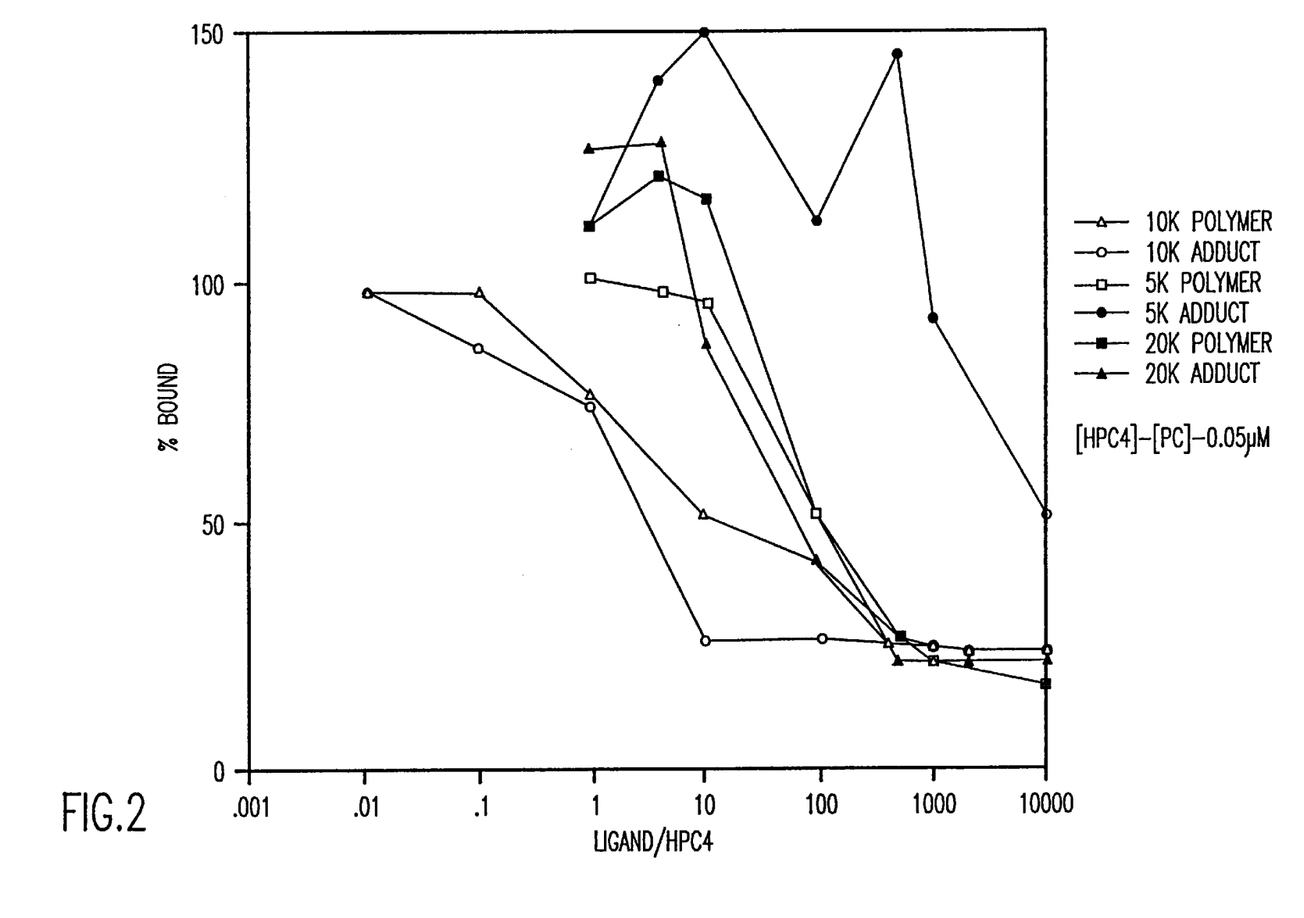
FIG. 2 is a graph comparing the activity of immunosorbents, prepared with varying molar ratios of poly(2-ethyloxazoline)-HCPC[6–17] adducts during masking procedures, with immunoabsorbents prepared without the use of an ODA.
Figure 3:
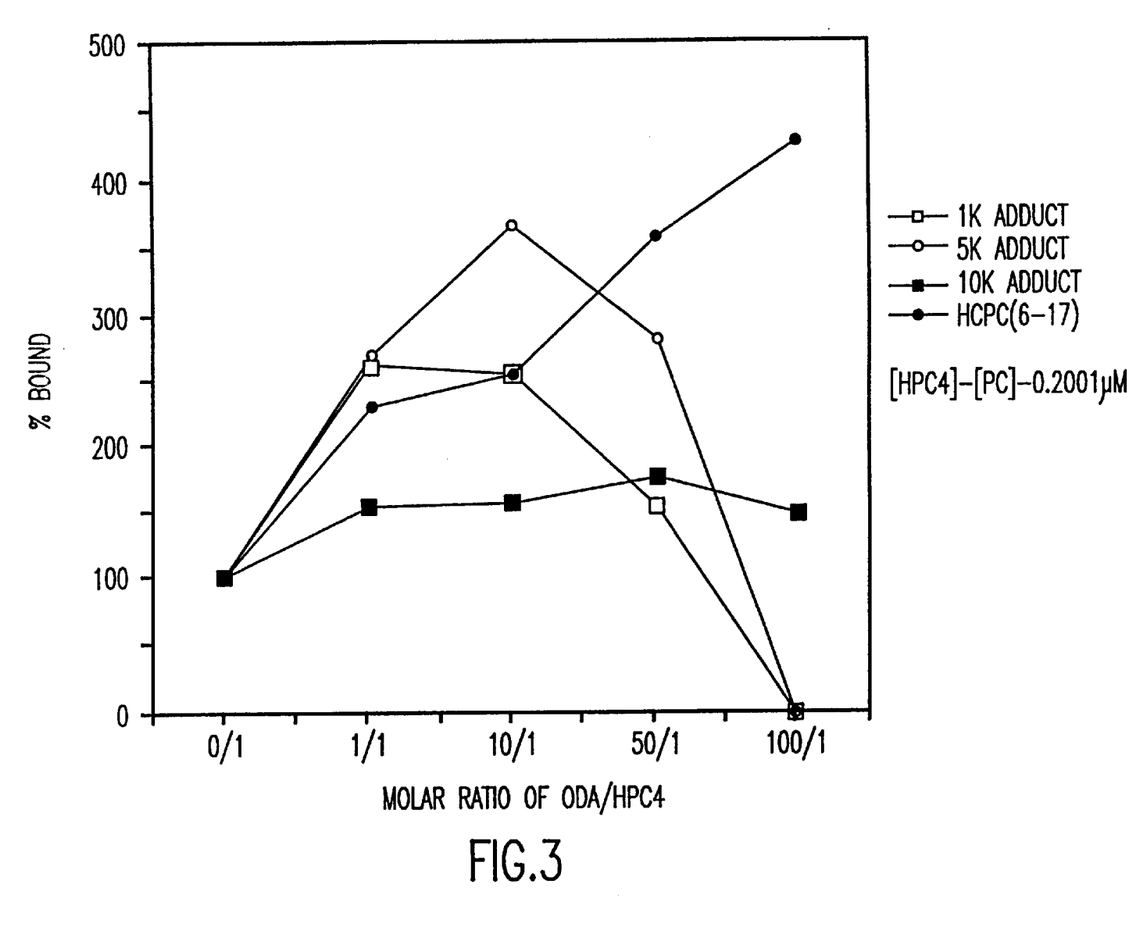
FIG. 3 is a graph comparing the activity of immunosorbents, prepared with varying molar ratios of poly(2-methyloxazoline)-HCPC[6–17] ODA to antibody during masking procedures, with immunosorbents compared without the use of an ODA.
Figure 4:
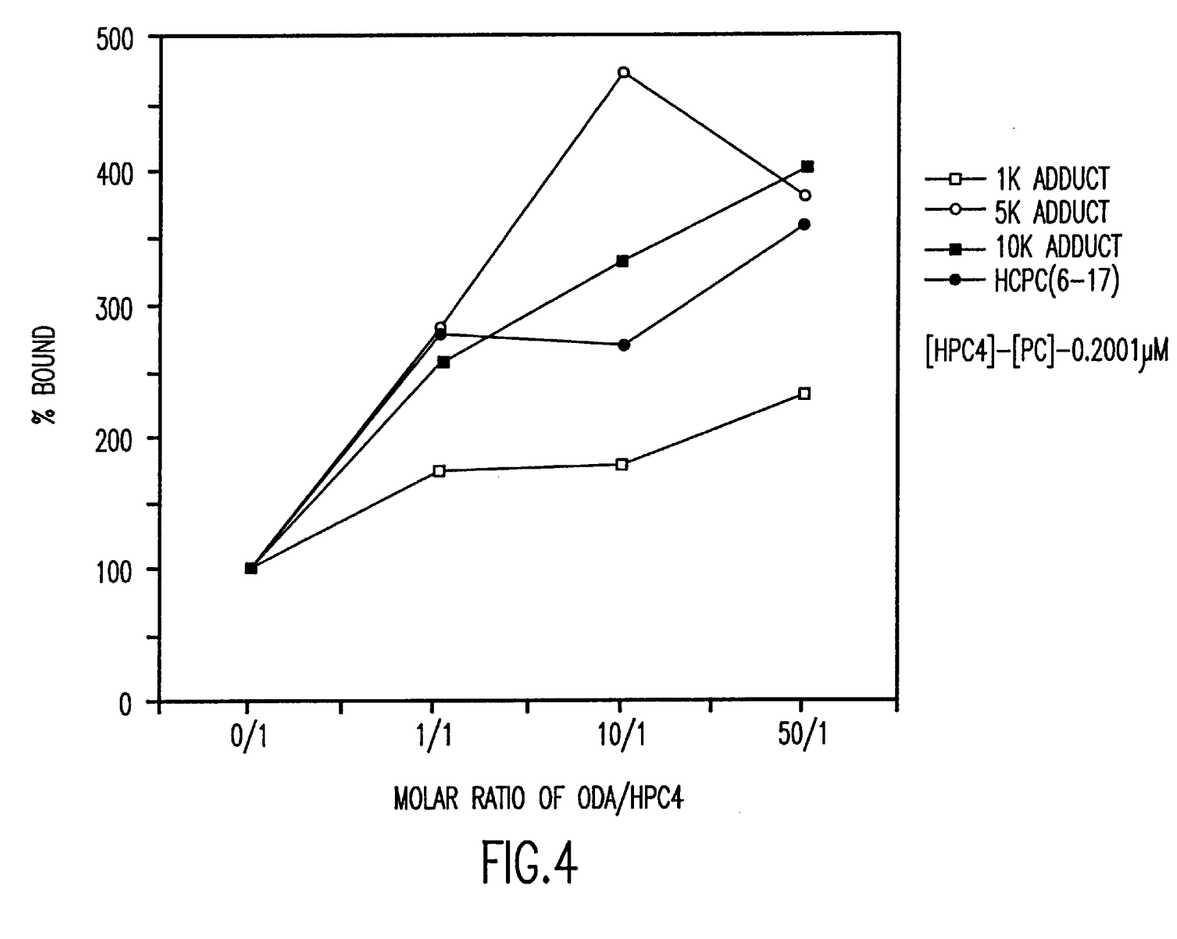
FIG. 4 is a graph of the data from FIG. 3, normalized with respect to loss of sites due to the presence of the ODA species.
Figure 5:
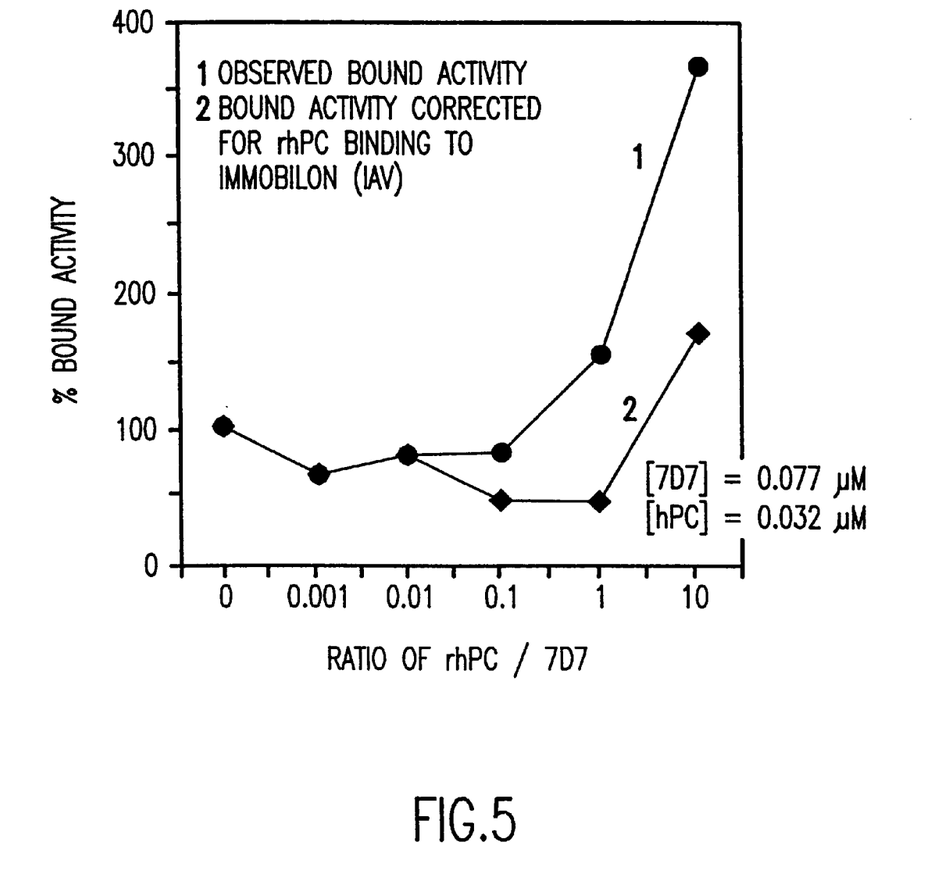
FIG. 5 is a graph comparing the activity of immunosorbents, prepared with varying molar ratios of recombinant human protein C prepared from *E. Coli* transvected with the cDNA of human protein C, rhPC, ODA to 77B10 antibody (murine monoclonal antibody against hPC) during masking procedures, with immunosorbents prepared without the use of an ODA.
Figure 6:
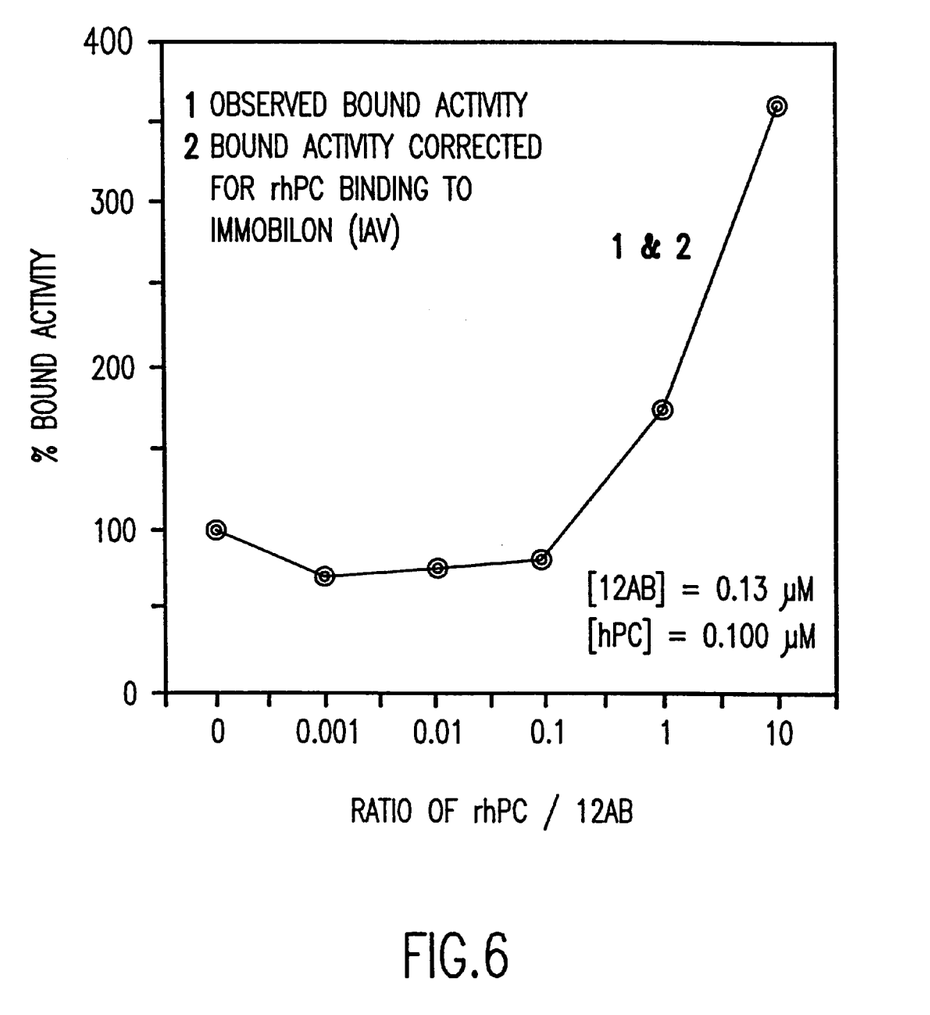
FIG. 6 is a graph comparing the activity of immunosorbents, prepared with varying molar ratios of rhPC ODA to 12 A8 antibody (murine monoclonal antibody against hPC) during masking procedures, with immunosorbents prepared without the use of an ODA.
Figure 7:
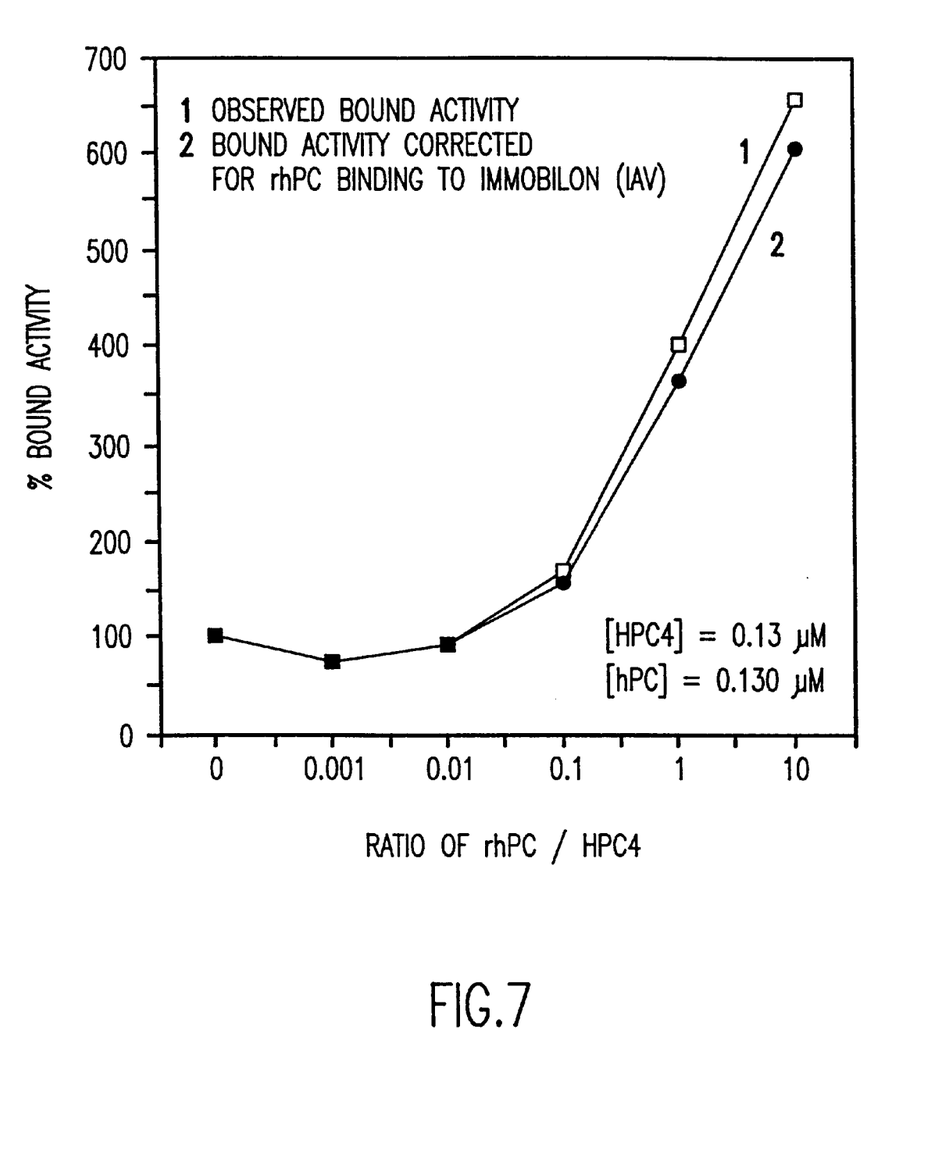
FIG. 7 is a graph comparing the activity of immunosorbents, prepared with varying molar ratios of rhPC ODA to HPC4 antibody during masking procedures, with immunosorbents prepared without the use of an ODA.

The effect of high molecular weight poly(2-ethyoxazoline)-peptide adducts on bound activity of immunosorbents prepared by using the ethyl-POX peptide adducts as ODAs, and binding of the masked HPC4-Mabs onto Immulon II surfaces was determined. 5K-, 10K and 20K poly(2-ethyloxazoline)-peptide adducts were prepared, and various molar ratios of the ethyl POX peptide adducts to HPC4-Mab were prepared. The bound activities of immunosorbents prepared with the ethyl POX-HPC4-Mab complexes were determined as described above. With reference to FIG. 2, the affect of the high molecular weight ethyl POX-peptide adducts on the bound activity of HPC4-Mabs on immulon 2 surfaces is graft. Note that none of the higher molecular weight ethyl POX-peptide adducts demonstrated a significant increase in bound activity. Note that the bound activities represented in FIGS. 1 and 2 require normalization to account for the loss of available sites due to binding of the POX polymer, POX-peptide adduct, and peptide directly to the support. For example, free HCPC(6–17)peptide results in thirty-four percent loss in antibody binding sites on the matrix, and 1K poly(2-ethyloxazoline)-peptide adduct reduces by twenty-three percent the amount of bound antibody on the Immulon II surfaces. This is because the Immulon II surfaces bind proteins through low energy forces, such as hydrophobic interactions. High molecular weight ODAs, such as the 10K-ethyl POX-peptide adduct are very hydrophobic, and competitively bind with the antibody to the Immulon II surface. Note that poly(2-methyloxazoline)peptide adducts and will generally not compete as strongly with the antibody for binding sites on the Immulon II surface.

Thus, it is clear that care must be taken in selecting the ODA to be used with particular surfaces, since in certain instances, such as the use of high molecular weight POX-peptide adducts with Immulon II surfaces, the percent bound activity of the resulting immunosorbent can actually be less than an immunosorbent prepared without the use of the ODA.

EXAMPLE 3

Poly(2-methyloxazoline)-peptide adducts, and HCPC (6–17) peptide were equilibrated with HPC4-Mab and immobilized on Immobilon(IAV) membranes. With reference to FIG. 3, the effect of the methyl-POX adducts and the HCPC(6–17) peptide on the bound activity of HPC4 on Immobilon membranes is illustrated. A maximum bound activity is achieved for the 5k-methyl-POX adduct, which has an activity 3.75 times greater than a non-ODA-oriented-HPC4-Mab applied to the membrane, as reflected by line 2. The 1k-adduct, represented by line 1, has a bound HPC4-Mab activity which is 2.6 times greater than the control immunosorbent, and the 10k-adduct, represented by line 3 has a bound activity as high as 1.5 times the bound activity of the control HPC4-Mab immunosorbent. Line 4 shows that molar ratios of 100/1 of HCPC(6–17) to HPC4-Mab in the masking of equilibration solution, result in an immunosorbent, using Immobilon as a support, having 4.3 times greater bound activity than the control HPC4-Mab immunosorbent made without the use of an ODA.

FIG. 4 is a graph of the data from FIG. 3, normalized with respect to loss of sites due to presence of the ODA species. Line 1 represents the 1k-adduct, line 2 represents the 5k-adduct, line 3 represents the 20k-adduct and line 4 represents the free HCPC(6–17)peptide. Note that when the data is normalized for the loss of sites, that all of the resulting immunosorbents demonstrate considerable increases in bound activities over immunosorbents prepared without the use of an ODA.

EXAMPLE 4

Using the general procedures outlined above, 7D7B10-$M_{AB}$ were immobilized on Immobilon membranes using rhPC as an ODA or FMA. With reference to FIG. 5, line 1 represents the observed bound activity, and line 2 represents the observed bound activity corrected for loss of sites due to rhPC binding to the Immobilon membrane. Note that with a molar ratio of rhPC to 7D7B10-MAB in the masking or equilibration step of 10, that the resulting immunosorbent has nearly double the bound activity of an immunosorbent prepared using 7D7B10-$M_{AB}$ without use of an ODA.

EXAMPLE 5

Immunosorbents were prepared using 12A8-Mab and rhPC as an ODA, followed by immobilization on Immobilon membranes. With reference to FIG. 6, the percent bound activity of the immunosorbents, prepared with rhPc OPA compared to immunosorbents, having bound 12A8-Mab immobilized without first using an ODA, is presented. Note that the observed bound activity, and the bound activity corrected for rhPC binding to Immobilon were indistinguishable at the rhPC/12A8 molar ratios in the masking or equilibration step. Note that the bound activity of the immunosorbent prepared using a molar ratio of rhPC/12A8 in the masking step has a bound activity more than three and one-half times greater than the bound activity of an immunosorbent having 12A8-MAB immobilized thereon without the use of an ODA.

EXAMPLE 6

HPC4-Mab was oriented on Immobilon membranes using rhPC as an ODA. With reference to FIG. 7, line 1 is the observed bound activity of the immunosorbents prepared in comparison to immunosorbents prepared without using the ODA. Line 2 corrects the observed bound activities in line 1 for the loss of sites due to rhPC binding to the Immobilon membranes. Note that nearly a six-fold increase in bound activity is possible using a molar ratio of rhPC to HPC4-Mab in the equilibration step in comparison to immunosorbents having Immobilon membranes as a support with HPC4-Mab immobilized thereon.

Thus, it is apparent that vast increases in the activity of antibodies bound to supports in immunosorbents can be obtained through the use of ODAs. One of skill in the art will recognize that different antibodies and different supports will require adjustment of the molar ratio of the ODA to the ligand or antibodies sought to be bound in the masking or equilibration step, so as to optimize the bound activity of the immunosorbent produced. Further, it has been demonstrated that synthetic epitopes and chimeric adducts of antigens or synthetic epitodes may be useful as ODAs, and can result in the production of immunosorbents having even greater bound activity than immunosorbents prepared with the "free" epitope or antigen.

Contemplated equivaletns of the immunosorbents of the present invention include any ligand or antibody immobilized on a support, such as a gel or membrane or any other suitable chromatographic support, such that a higher percentage of the antibodies immobilized on the support are oriented to be active in comparison to the random orientation of antibodies which were immobilized on a support in a random fashion. This improved bound activity of the immunosorbents of the present invention is achieved through the use of ODAs. Contemplated equivalents of the ODAs include any protein, hapten, or chimeric adduct of a protein or antigen.

From the above teachings, it is apparent that many modifications and variations of the present invention are possible. It is therefore to be understood that the invention may be practiced otherwise than as specifically described.

2. A process for producing an immunosorbent according to claim 1 further comprising a step of:
  removing said ODA from said immobilized ODA-antibody complex to form an immunosorbent wherein said antitope of said antibody is oriented away from said support and said antibody maintains avidity.

3. A process for producing an immunosorbent comprising the steps of:
  a) masking an $F_{ab}$ region of an antibody with an Orientation Directing Agent; and
  b) immobilizing said masked antibody on a support such that said $F_{ab}$ region of said antibody is oriented away from said support.

4. A process according to claim 3 further comprising the step of:
  removing said Orientation Directing Agent from said immobilized antibody to produce an immunosorbent having immobilized antibody oriented away from the support and wherein said antibody retains avidity.

5. A process according to claim 3 wherein said Orientation Directing Agent is selected from the group consisting of proteins, haptens, antigens, and chimeric adducts of polymers with an antigen.

6. A process according to claim 5 wherein said immobilization step is carried out by binding a first protein to said support to form an immobilized protein:
  binding a second protein to a masked antibody, said second protein having an affinity for said immobilized protein;
  binding said second protein bound to said masked antibody to said immobilized protein.

---

---

We claim:

1. A process for producing an immunosorbent comprising:
  a) masking an antitope of an antibody with an Orientation Directing Agent (ODA) to form an ODA-antibody complex; and
  b) immobilizing the ODA-antibody complex on a support such that the ODA-masked antitope is oriented away from said support.

7. A process according to claim 6 wherein said first and second proteins are different from each other, and are selected from the group consisting of avidin, protein A, immunoglobulin, and protein G.

8. The process of claim 2 wherein the ODA is an antigen.

9. The process of claim 4 wherein the Orientation Directing Agent is an antigen.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 12 amino acids
      (B) TYPE: amino acid
      (D) TOPOLOGY: linear    (ii) MOLECULE TYPE: peptide    (iii) HYPOTHETICAL: N    (v) FRAGMENT TYPE: internal    (vi) ORIGINAL SOURCE:
      (A) ORGANISM: HCPC[6-17] EPITOPE FOR HUMAN PROTEIN C    (xi) SEQUENCE DESCRIPTION: SEQ ID NO:1:

```
Glu Asp Gln Val Asp Pro Arg Leu Ile Asp Gly Lys
1               5                   10
```